United States Patent
DeVincenzo

(10) Patent No.: US 7,850,450 B2
(45) Date of Patent: Dec. 14, 2010

(54) ORTHODONTIC BONE ANCHOR

(76) Inventor: John DeVincenzo, 1312 Garden St., San Luis Obispo, CA (US) 93401; John Peter DeVincenzo, III, legal representative, 7250 Waverly Rd., Proctor, AR (US) 72376

( * ) Notice: Subject to any disclaimer, the term of this patent is extended or adjusted under 35 U.S.C. 154(b) by 459 days.

(21) Appl. No.: 11/268,053

(22) Filed: Nov. 8, 2005

(65) Prior Publication Data

US 2007/0123882 A1    May 31, 2007

(51) Int. Cl.
*A61C 3/00* (2006.01)
(52) U.S. Cl. ......................................................... 433/18
(58) Field of Classification Search .................. 433/18, 433/172–177, 180–181
See application file for complete search history.

(56) References Cited

U.S. PATENT DOCUMENTS

| 4,054,996 | A  | * | 10/1977 | Wallshein ....................... 433/7 |
| 5,222,942 | A  | * | 6/1993  | Bader .......................... 604/110 |
| 5,853,291 | A  | * | 12/1998 | DeVincenzo et al. ......... 433/176 |
| 6,183,250 | B1 | * | 2/2001  | Kanno et al. ................... 433/17 |
| 2002/0150856 | A1 | * | 10/2002 | Payton .......................... 433/8 |
| 2004/0166461 | A1 | * | 8/2004  | Devincenzo .................. 433/18 |
| 2005/0147938 | A1 | * | 7/2005  | Devincenzo et al. .......... 433/18 |

* cited by examiner

*Primary Examiner*—Cris L Rodriguez
*Assistant Examiner*—Heidi M Eide
(74) *Attorney, Agent, or Firm*—Rodgers & Rodgers

(57) ABSTRACT

An orthodontic bone anchor comprising an anchor plate, a tube affixed to the emerging end of the anchor plate and, a rod slidable within the tube, a groove formed in the rod, a plate attached to the tube at one end and having a V-shaped notch at the other end, and the V-shaped notch adapted to cooperate with the groove to prevent movement of the rod with respect to the tube.

7 Claims, 1 Drawing Sheet

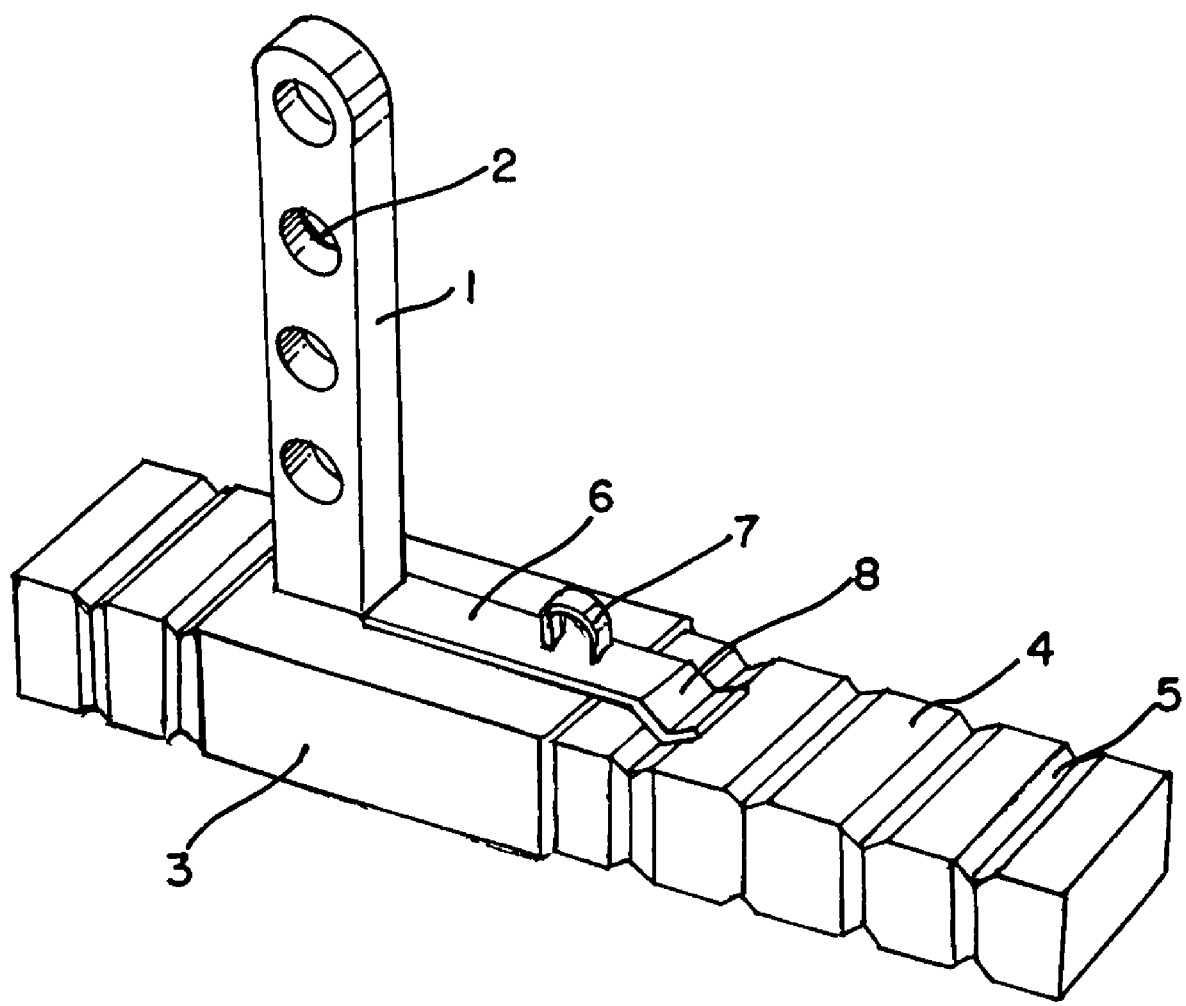

ORTHODONTIC BONE ANCHOR

BACKGROUND OF THE INVENTION

In orthodontics, typically an anchor plate is screwed to a patient's bone and extends into the vestibule from which elastomeric material or springs are attached to facilitate movement of the patient's teeth. The disadvantage to this is that the point of force application cannot be changed during treatment nor can the bone anchor be modified or adjusted prior to insertion or during treatment. A change in the location of force application to the dentition is often required and without a corresponding change on the anchor, a different and generally undesirable change in the vector of force occurs. In addition, the surgeon often encounters difficulty in placing the anchor plate as distally as desired.

SUMMARY OF THE INVENTION

An anchor plate is secured to a patient's bone with an angular tube secured to the emerging end thereof, a corresponding angular rod is inserted through the tube and multiple grooves are formed in the rod. In addition, a plate is adhered to the tube at one end thereof and is adapted to flex either vertically or horizontally depending on where the plate is placed. A V-shaped notch is formed on the distal end of the plate and adapted to cooperate with the grooves formed in the rod and allow the rod to be incrementally extended with respect to the tube.

DESCRIPTION OF THE DRAWING

The single view drawing is a perspective view of the orthodontic bone anchor according to this invention.

DETAILED DESCRIPTION OF THE INVENTION

In the drawing, anchor plate 1 is shown which is attached to a patient's bone by means of screws inserted through apertures 2. Quadrilateral tube 3 is secured to the emerging end of anchor plate 1 by any suitable means such as welding and quadrilateral rod 4 is insertable through hollow tube 3, as shown in the drawing. In addition, multiple V-shaped grooves 5 extend around the periphery of rod 4.

According to a feature of this invention, resilient plate 6 is attached to the outer surface of tube 3 adjacent anchor plate 1 by suitable means such as welding and the like. Also, loop or hook 7 is attached to the upper surface of plate 6 by means such as welding. Finally, a V-shaped notch 8 is formed on the free end of plate 6 and extends beyond the adjacent end of tube 3 and is adapted to selectively nest in locking engagement with grooves 5.

In practice, anchor plate 1 is secured to a patient's bone by means of screws inserted through apertures 2 as is well known. Then, depending on the desired location and direction of the force vector, plate 6 is lifted by grasping loop 7 by means of an appropriate instrument and lifting plate 6 such that rod 4 is maneuverable through tube 3 to the desired position as determined by the clinician. Loop 7 is then released and plate 6 springs downwardly so as to allow V-shaped notch 8 to nest with whichever one of the grooves 5 is disposed therebelow. By this means, rod 4 is, in effect, locked in place. Following this, appropriate elastomeric material or springs are placed around the appropriate groove 5 for optimum force application.

As an alternative, anchor plate 1 can be bent through an arc of 90 degrees so as to achieve an alternative disposition of rod 4 depending on the force requirements of the particular patient.

Therefore, by this invention, a bone anchor is provided which is adjustable to allow multiple points of vertical force application from a single bone anchor without the necessity of multiple bone anchors, the need to move the anchor from one location to another, and with lessened demand on the part of the surgeon to place the bone anchor in a precise location.

The invention claimed is:

1. An orthodontic bone anchor comprising an anchor plate, a hollow angular tube affixed to one end thereof, an angular rod slidable within said angular tube, a plate resiliently affixed at one end thereof to said angular tube, said plate having a free end, a V-shaped notch formed on said free end of said plate, said V-shaped notch extending beyond one end of said angular tube, multiple V-shaped grooves formed in said angular rod to nest in selective locking engagement with said V-shaped notch and to provide varying attachment points for orthodontic appliances, and means for manually grasping and lifting said plate to allow sliding movement of said angular rod within said angular tube.

2. An orthodontic bone anchor according to claim 1 wherein said groove extends around the periphery of said angular rod.

3. An orthodontic bone anchor according to claim 1 wherein said grasping and lifting means comprises a loop or hook directly affixed to the surface of said plate opposite said angular tube.

4. An orthodontic bone anchor according to claim 3 wherein said plate is attached to said angular tube adjacent to said anchor plate.

5. An orthodontic bone anchor according to claim 1 wherein said plate comprises upper and lower surfaces and said lower surface is at least partially in face contacting relation with said angular tube.

6. An orthodontic bone anchor according to claim 1 wherein said angular tube and said angular rod are quadrilateral in configuration.

7. An orthodontic bone anchor according to claim 1 wherein said anchor plate is bendable.

* * * * *